US009863871B2

(12) United States Patent
Tagawa et al.

(10) Patent No.: US 9,863,871 B2
(45) Date of Patent: Jan. 9, 2018

(54) ILLUMINATION DEVICE FOR COLOR SORTER (71) Applicant: Satake Corporation, Tokyo (JP)

(72) Inventors: Sumio Tagawa, Hiroshima (JP);
Teruhiko Takeuchi, Hiroshima (JP);
Hidenobu Kado, Hiroshima (JP)

(73) Assignee: SATAKE CORPORATION, Tokyo (JP)

( * ) Notice: Subject to any disclaimer, the term of this patent is extended or adjusted under 35 U.S.C. 154(b) by 0 days.

(21) Appl. No.: 15/029,341

(22) PCT Filed: Sep. 9, 2014

(86) PCT No.: PCT/JP2014/073778
§ 371 (c)(1),
(2) Date: Apr. 14, 2016

(87) PCT Pub. No.: WO2015/056501
PCT Pub. Date: Apr. 23, 2015

(65) Prior Publication Data
US 2016/0274021 A1 Sep. 22, 2016

(30) Foreign Application Priority Data

Oct. 17, 2013 (JP) .................................. 2013-216367
Oct. 17, 2013 (JP) .................................. 2013-216368

(51) Int. Cl.
G01N 21/35 (2014.01)
G01N 21/25 (2006.01)
(Continued)

(52) U.S. Cl.
CPC ............ *G01N 21/255* (2013.01); *B07C 5/342* (2013.01); *G01N 21/35* (2013.01); *G01N 21/85* (2013.01)

(58) Field of Classification Search
CPC ....... G01N 21/255; G01N 21/35; B07C 5/342
See application file for complete search history.

(56) References Cited

U.S. PATENT DOCUMENTS 4,919,534 A * 4/1990 Reed .................... B07C 5/3416
209/524
5,956,413 A * 9/1999 Oste .................... B07C 5/3425
382/110
(Continued)

FOREIGN PATENT DOCUMENTS

JP H08229517 A 9/1996
JP 11051845 2/1999
(Continued)

OTHER PUBLICATIONS

Machine translations for JP-11-051845 A, JP 3163443 U, JP 2012-164541 A and JP 2003-163090 A.*
(Continued)

Primary Examiner — David Porta
Assistant Examiner — Djura Malevic
(74) Attorney, Agent, or Firm — Orion Consulting, Ltd.; Joseph P. Farrar, Esq.

(57) ABSTRACT

An illumination device for a color sorter includes an LED substrate placed on a longitudinal chassis for heat radiation and a light source in which many LED elements are linearly aligned in the longitudinal direction on the LED substrate, and the light source is an integration of at least two light sources provided together, one of the light sources illuminating a side on which items-to-be-sorted flow down and the other one of the light sources illuminating a side of a background arranged to face a camera.

4 Claims, 6 Drawing Sheets (51) Int. Cl.
  *B07C 5/342* (2006.01)
  *G01N 21/85* (2006.01)

(56) References Cited

U.S. PATENT DOCUMENTS

| | | | | |
|---|---|---|---|---|
| 6,013,887 A * | 1/2000 | Satake | B07C 5/3425 | 209/580 |
| 6,060,677 A * | 5/2000 | Ulrichsen | B07C 5/342 | 209/577 |
| 6,078,018 A * | 6/2000 | Davis | B07C 5/3416 | 209/580 |
| 6,250,774 B1 * | 6/2001 | Begemann | F21S 8/086 | 362/231 |
| 6,373,573 B1 * | 4/2002 | Jung | A61B 5/0075 | 347/19 |
| 6,914,678 B1 * | 7/2005 | Ulrichsen | B07C 5/342 | 356/429 |
| 7,113,272 B2 * | 9/2006 | Bourely | B07C 5/342 | 356/237.1 |
| 7,816,616 B2 * | 10/2010 | Kenny | B07C 5/342 | 209/576 |
| 7,997,770 B1 * | 8/2011 | Meurer | F21K 9/27 | 362/171 |
| 8,422,003 B2 * | 4/2013 | Hartrumpf | B07C 5/3425 | 356/445 |
| 8,907,241 B2 * | 12/2014 | Dell'Endice | B07C 5/02 | 209/576 |
| 2002/0060526 A1 * | 5/2002 | Timmermans | H05B 33/0803 | 315/246 |
| 2005/0046850 A1 * | 3/2005 | Chow | G01B 11/0625 | 356/430 |
| 2005/0279949 A1 * | 12/2005 | Oldham | F21K 9/00 | 250/458.1 |
| 2006/0016735 A1 * | 1/2006 | Ito | B07C 5/366 | 209/576 |
| 2006/0181708 A1 * | 8/2006 | Takahashi | G01N 21/171 | 356/432 |
| 2007/0158245 A1 * | 7/2007 | Kenny | B07C 5/342 | 209/576 |
| 2009/0140271 A1 * | 6/2009 | Sah | F21V 31/04 | 257/88 |
| 2010/0193412 A1 * | 8/2010 | MacK, Jr. | B07C 5/342 | 209/585 |
| 2010/0230327 A1 * | 9/2010 | Hartrumpf | B07C 5/3425 | 209/577 |
| 2011/0303928 A1 * | 12/2011 | Kawabata | F21K 9/17 | 257/88 |
| 2011/0317001 A1 * | 12/2011 | Massen | B07C 5/3425 | 348/91 |
| 2012/0049203 A1 * | 3/2012 | Mondada | H01L 25/0753 | 257/88 |
| 2013/0069089 A1 * | 3/2013 | Hussell | F21V 3/00 | 257/88 |
| 2013/0168301 A1 * | 7/2013 | Dell'Endice | B07C 5/02 | 209/587 |
| 2013/0258668 A1 * | 10/2013 | Dellian | F21V 17/08 | 362/249.02 |
| 2014/0151731 A1 * | 6/2014 | Tran | H01L 33/50 | 257/98 |

FOREIGN PATENT DOCUMENTS

| | | |
|---|---|---|
| JP | 2000107703 A | 4/2000 |
| JP | 2002199837 A | 7/2002 |
| JP | 2003163090 A | 6/2003 |
| JP | 2008519266 A | 6/2008 |
| JP | 3163442 U | 10/2010 |
| JP | 2011014389 A | 1/2011 |
| JP | 2011086602 A | 4/2011 |
| JP | 2012164541 A | 8/2012 |

OTHER PUBLICATIONS

Machine copy and translation of JP 11-051845, AJP 3163443 U and JP 2003-163090 A.*
International Search Report for Application No. PCT/JP2014/073778 dated Nov. 4, 2014.

* cited by examiner

ILLUMINATION DEVICE FOR COLOR SORTER

CROSS-REFERENCE TO RELATED APPLICATION

The present application is a national phase entry under 35 U.S.C. §371 of International Application No. PCT/JP2014/073778, filed Sep. 9, 2014, which claims priority from Japanese Application No. 2013-216367, filed Oct. 17, 2013 and Japanese Application No. 2013-216368, filed Oct. 17, 2013, all of which are incorporated herein by reference.

TECHNICAL FIELD

The invention relates to improvement of an illumination device for a color sorter, and in particular, seeks to reduce the number of illumination means installed inside an optical detection part for downsizing thereof. Moreover, the invention provides a long-life and low-power illumination device capable of maintaining stable luminance.

BACKGROUND ART

Conventionally, as a device for causing particle matters, which become items-to-be-sorted, to flow down and irradiating the flowing-down particle matters with light, detecting color difference or brightness difference by sensors to detect unacceptable items, which are discolored to colors different from colors of acceptable items, or foreign matters, and distinguishing the unacceptable items or foreign matters from the flow of acceptable items to eliminate thereof, a color sorter has been known (for example, refer to Patent Literature 1).

This kind of color sorter is based on a principle that the items-to-be-sorted are irradiated with light from a light source, color difference, brightness difference or the like of reflected light from the items-to-be-sorted or light transmitted through the items-to-be-sorted is detected by a sensor, and based on the color difference or brightness difference, unacceptable items or foreign matters admixed to the items-to-be-sorted are immediately eliminated by an ejector. As a sensor to be adopted, to increase sorting yield, a line sensor configured with a line CCD, which is linear and capable of simultaneous detecting, is used in many cases; as a light source for a sensor like this, in a conventional color sorter, a fluorescent lamp of a straight tube or an array of many halogen bulbs or LED elements has been used (for example, refer to Patent Literature 2, FIG. 9).

Then, the sorter is configured to set plural straight tube fluorescent lamps or linear LED elements with different wavelengths in accordance with the items-to-be-sorted or foreign matters to be the target in the optical detection part, to thereby illuminate each of a side on which the items-to-be-sorted, such as grains, flow down and a proximity of a background, such as a reflective plate; therefore, conventionally, there has been a need for installing plural illumination means in the optical detection part (refer to Patent Literature 2, paragraph 0043, FIG. 4).

Moreover, this kind of color sorter is based on a principle that the items-to-be-sorted are irradiated with light from a light source, color difference, brightness difference or the like of reflected light from the items-to-be-sorted or transmitted light through the items-to-be-sorted is detected by a sensor, and based on the color difference or brightness difference, unacceptable items or foreign matters admixed to the items-to-be-sorted are immediately eliminated by an ejector. As a sensor to be adopted, to increase sorting yield, a line sensor configured with a line CCD, which is linear and capable of simultaneous detecting, is used in many cases; as a light source for a sensor like this, in a conventional color sorter, a fluorescent lamp of a straight tube or an array of many halogen bulbs or LED elements has been used (for example, refer to Patent Literature 3, FIG. 9).

CITATION LIST

Patent Literature

Patent Literature 1: Japanese Patent Laid-Open No. 8-229517
Patent Literature 2: Japanese Patent Laid-Open No. 2000-107703
Patent Literature 3: Japanese Patent Laid-Open No. 2011-14389

SUMMARY OF THE INVENTION

Technical Problem

In consideration of the above problems, it is an object of the invention to provide an illumination device for a color sorter capable of reducing the number of illumination means installed in an optical detection part and downsizing thereof. Moreover, it is an object of the invention to provide a compact illumination device for a color sorter, which is excellent in long-life and low-power properties.

Solution to Problem

To solve the above problems, an illumination device for a color sorter according to the invention includes a longitudinal chassis for heat radiation, an LED substrate placed on the chassis, and a light source in which many LED elements are linearly aligned in a longitudinal direction on the LED substrate, and the light source is an integration of at least two light sources provided together, and one of the light sources illuminates a side on which items-to-be-sorted flow down and the other one of the light sources illuminates a side of a background arranged to face a camera of the color sorter.

In the two light sources, one of the light sources may be a light source that emits light in a wavelength range of visible light, and the other one of the light sources may be a light source that emits light in a wavelength range of near-infrared light.

A shape of the chassis on which the LED substrate is placed may be a triangular roof shape in a cross section, and one of inclined surfaces of the triangular roof shape may be formed as the light source for illuminating the side on which the items-to-be-sorted flow down and the other one of the inclined surfaces may be formed as the light source for illuminating the background.

In the LED substrate, while an illuminance sensor is provided adjacent to the LED element, a control device that keeps illuminance of the light source constant based on illuminance data from the illuminance sensor may be provided.

An illumination device for a color sorter according to the invention includes a longitudinal chassis for heat radiation, an LED substrate placed on the chassis, and a light source in which many LED elements are linearly aligned in a longitudinal direction on the LED substrate, and, in the LED substrate, while an illuminance sensor is provided adjacent to the LED element, a control device that keeps illuminance of the light source constant based on illuminance data from the illuminance sensor is provided.

In the LED substrate, a temperature sensor that detects a temperature of the LED element is provided near the illuminance sensor.

Advantageous Effects of the Invention

The illumination device for a color sorter according to the invention includes a light source arranged at the optical detection part of the color sorter, which is an integration of at least two light sources together, and one of the light sources illuminates a side on which the items-to-be-sorted flow down and the other one of the light sources illuminates a background side arranged to face a camera. This makes it possible to double the light source that illuminates the side on which the items-to-be-sorted flow down and the light source that illuminates the background, and to reduce the number of light sources installed in the optical detection part.

If one of the light sources is formed as a light source that emits light in a wavelength region of visible light and the other one of the light sources is formed as a light source that emits light in a wavelength region of near-infrared light, it is possible to double the light source for the visible light and the light source for the near-infrared light, and therefore, the number of light sources installed in the optical detection part can be reduced.

By forming the shape of the chassis, on which the LED substrate is placed, as a triangular roof shape in a cross section, one of inclined surfaces of the triangular roof shape is used for the light source for illuminating the side on which the items-to-be-sorted flow down and the other one of inclined surfaces is used for the light source for illuminating the background arranged to face the camera, and thereby, it becomes possible to downsize the shared light source and to make the shared light source less costly.

Even though the light source is such that many LED elements are linearly aligned in the longitudinal direction on the LED substrate, since the LED substrate is installed on the longitudinal chassis for heat radiation, the LED substrate has high heat radiation effect and is less likely to be out of order. Moreover, in the LED substrate, while an illuminance sensor was provided adjacent to the LED element, a control device for keeping illuminance of the light source constant based on illuminance data from the illuminance sensor was provided, and therefore it became possible to resolve troubles, such as destabilization of illuminance or excessive increase in output, due to the illuminance of the light source kept constant based on the illuminance data from the illuminance sensor. This makes it possible to provide the illumination device excellent in long-life and low-power properties.

In the LED substrate, by providing, near the illuminance sensor, a temperature sensor that detects the temperature of the LED elements, accuracy in making the illuminance constant is improved. In other words, if control of increasing the illuminance based on the data from the illuminance sensor is performed, the temperature of the LED elements rises in proportion to increase of the current. At this time, since the temperature sensor operates, it becomes possible to suppress the rise of the current within an applicable temperature range of the LED elements.

DESCRIPTION OF EMBODIMENTS

Figure 1:
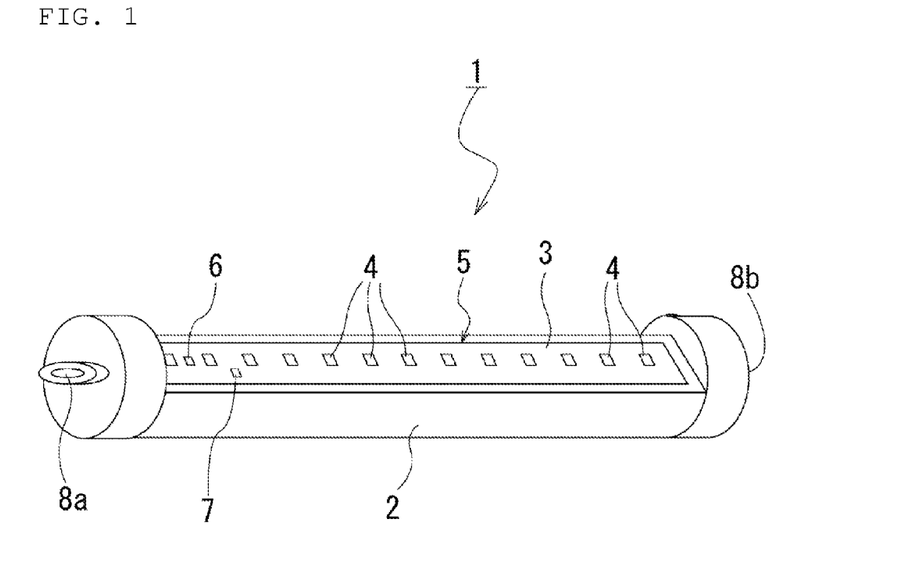
FIG. 1 is a schematic perspective view when an illumination cover of an illumination device is detached in an embodiment according to the invention.
Figure 2:
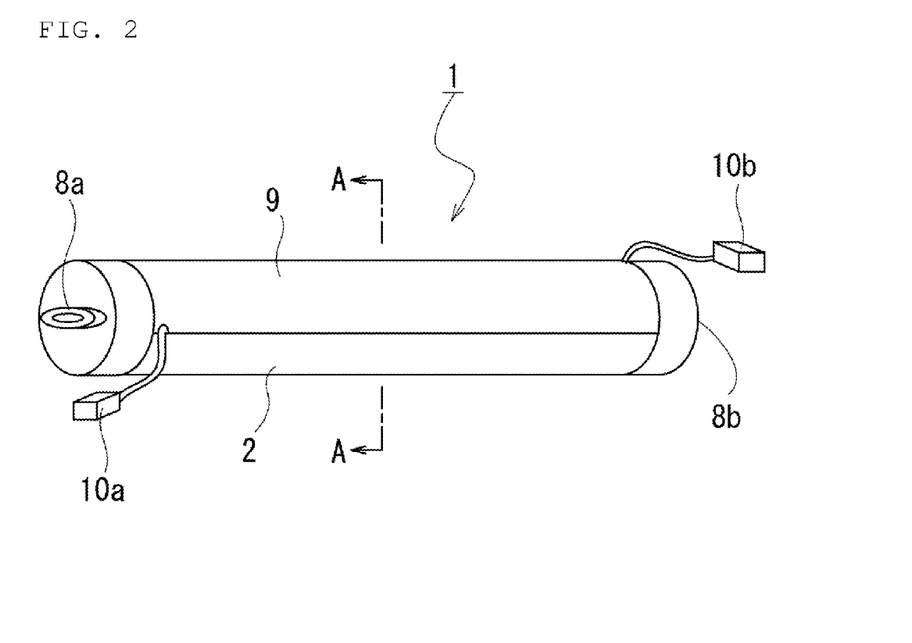
FIG. 2 is a schematic perspective view when the illumination cover of the illumination device, which is the same as above, is attached.
Figure 3:
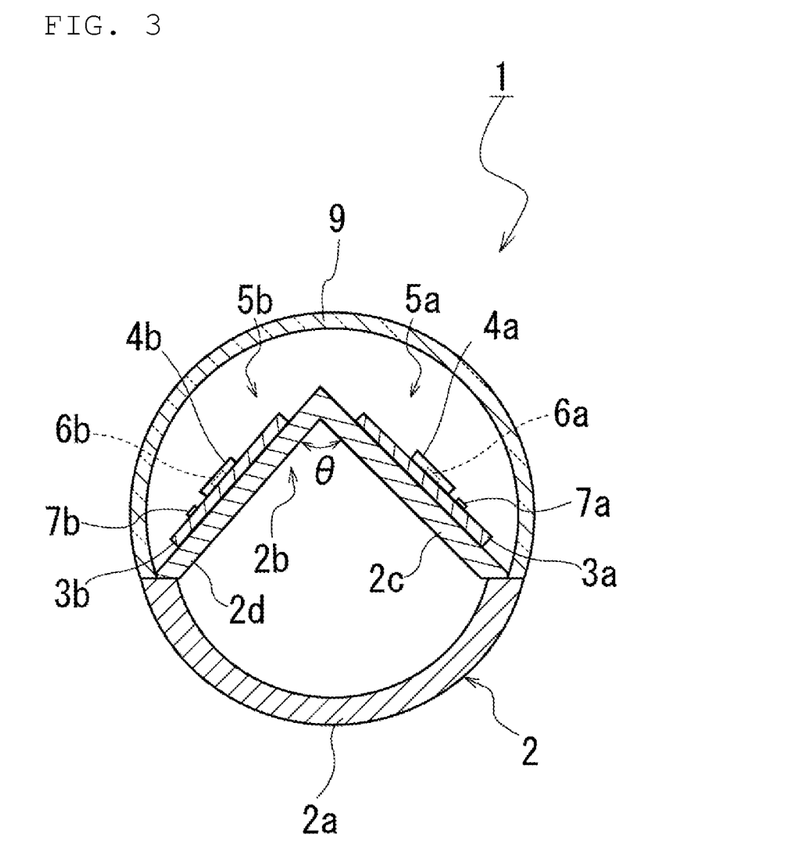
FIG. 3 is a schematic cross-sectional view showing an internal configuration of the illumination device, which is the same as above.

FIG. 1 is a schematic perspective view when an illumination cover of an illumination device is detached in an embodiment according to the invention, FIG. 2 is a schematic perspective view when the illumination cover of the illumination device is attached in the same as above, and FIG. 3 is a schematic cross-sectional view showing an internal configuration of the illumination device in the same as above.

As shown in FIG. 1, an illumination device 1 of the embodiment includes: a heat-radiating longitudinal chassis 2; an LED substrate 3 installed on the chassis; a light source 5 in which many LED elements 4 are linearly aligned in the longitudinal direction on the LED substrate 3; an illuminance sensor 6 provided adjacent to the LED elements 4 of the light source 5; a temperature sensor 7 provided near the illuminance sensor 6; and LED lamp sockets 8a and 8b for supplying power provided at both ends of the chassis 2. As a material of the longitudinal chassis 2, aluminum is suitable.

FIG. 2 shows, in addition to the illumination device 1 of FIG. 1, an illumination part cover 9 that is semi-translucent and made of white polycarbonate and sensor connectors 10a and 10b for the illuminance sensor 6 and the temperature sensor 7 being provided.

Then, FIG. 3 is an A-A fracture cross-sectional view of FIG. 2, which shows an internal configuration of the illumination device 1. With reference to FIG. 3, the chassis 2 is configured with a first chassis 2a having a cross section in U shape and a second chassis 2b placed on the first chassis 2a and having a cross section in a triangular roof shape. In the second chassis 2b, the light sources 5a and 5b are arranged on an inclined surface 2c forming the triangular roof shape and another inclined surface 2d forming the triangular roof shape, respectively.

In other words, the light source 5 is an integration of at least two light sources 5a and 5b provided together; the light source 5a on one of inclined surfaces 2c serves as a foreground illumination, that is, a light source for illuminating a side of the color sorter on which the items-to-be-sorted, such as grains, flow down, and the light source 5b on the other one of inclined surfaces 2d serves as a background illumination, that is, a light source for illuminating a background plate arranged to face a camera of the color sorter. Conversely, it is possible to use the light source 5a as the background illumination and the light source 5b as the foreground illumination. Then, if one of the light sources 5a is formed as a light source that emits light in a wavelength range of visible light, for example, 450 nm to 600 nm, and the other one of light sources 5b is formed as a light source that emits light in a wavelength range of near-infrared light, for example, 800 nm to 1300 nm, the light source 5 is able to double the light source for visible light and the light source for near-infrared light.

The angle of an internal angle θ of the triangular roof shape of the second chassis 2b is set in accordance with arrangement of an optical system of the color sorter, and may be in the range of, for example, about 80° to about 100°, preferably in the range of 85° to 95°, and more preferably in the range of 85° to 90°. Note that the shape of the second chassis 2b is not limited to the triangular roof shape and may be formed in, for example, a trapezoidal shape or a semicircular shape; the shape may be appropriately set in accordance with the shape of the optical detection part.

Further, to describe regarding FIG. 3, many LED elements 4a are linearly aligned in the longitudinal direction on the LED substrate 3a for the light source 5a (refer to FIG. 1), and an illuminance sensor 6a and a temperature sensor 7a are arranged adjacent to the LED element 4a. In a similar way, many LED elements 4b are linearly aligned in the longitudinal direction on the LED substrate 3b for the light source 5b, and the illuminance sensor 6b and the temperature sensor 7b are arranged adjacent to the LED element 4b.

Figure 4:
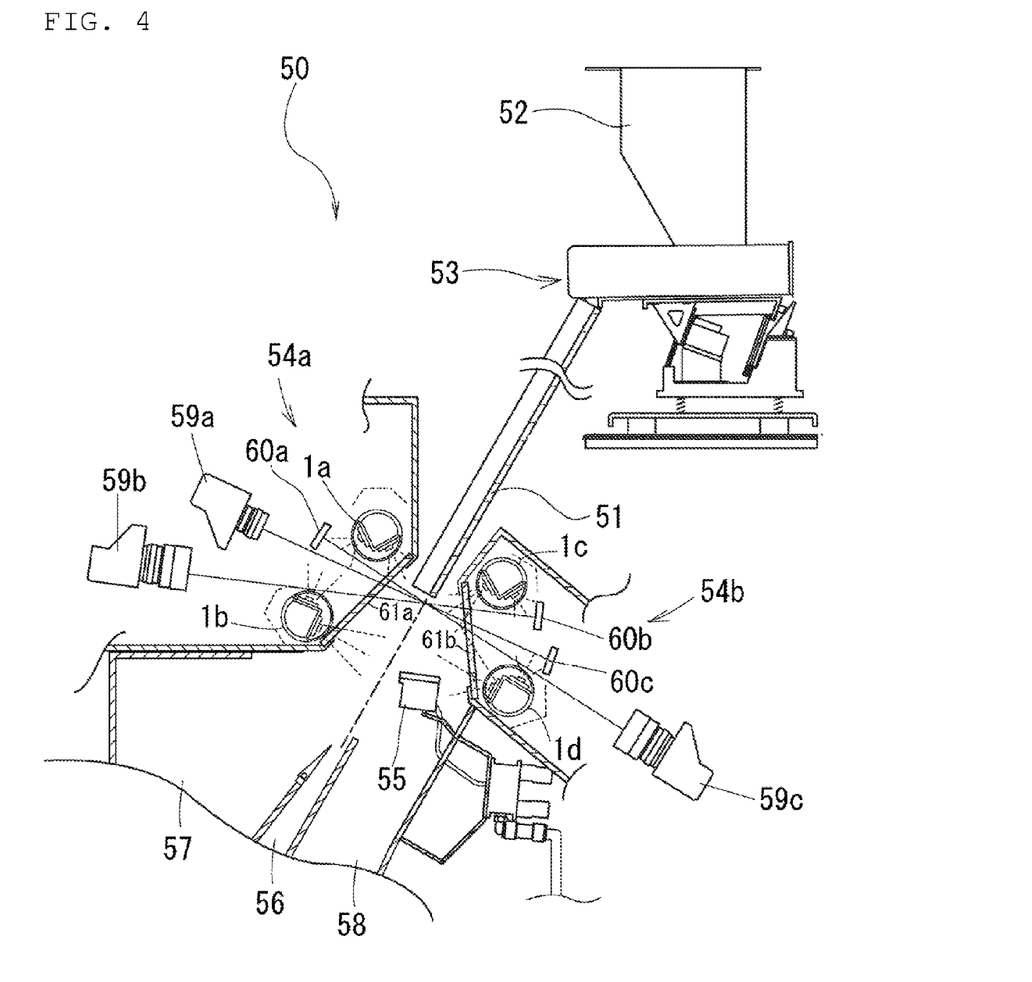
FIG. 4 is a schematic cross-sectional view when the illumination device, which is the same as above, is applied to a color sorter.

FIG. 4 is a schematic cross-sectional view when the illumination device is applied to a color sorter. As shown in FIG. 4, a color sorter 50 includes: a chute 51, as transfer means, arranged with inclination at an angle of about 60 degrees from the horizontal position; a storage tank 52 that stores the items-to-be-sorted, such as grains; a vibrating feeder 53 for feeding the items-to-be-sorted to the chute 51 from the storage tank 52; optical detection parts 54a and 54b vertically provided with a falling trajectory of the items-to-be-sorted interposed therebetween, the items-to-be-sorted falling from a lower end of the chute 51; an ejector nozzle 55 provided further below; an acceptable item recovery trough 56 provided below the ejector nozzle 55 on the same inclined line as the chute 51 to receive particle matters on the falling trajectory not being affected by spewed air from the ejector nozzle 55; an unacceptable item recovery trough 57 for recovering unacceptable grains from the normal items-to-be-sorted, the unacceptable grains being affected by the spewed air from the ejector nozzle 55; and an auxiliary unacceptable item recovery trough 58 for recovering unacceptable grains that failed to receive the spewed air from the ejector nozzle 55, hit surrounding members and were bounced back.

In the optical detection part 54a on the front side, plural cameras 59a and 59b, illumination devices 1a, 1b, and a facing background 60a are arranged. On the other hand, in the optical detection part 54b on the rear side, a single camera 59c, illumination devices 1c, 1d, and facing backgrounds 60b and 60c are arranged. Then, window members 61a and 61b formed of transparent glass are fitted into the optical detection parts 54a and 54b on the falling trajectory side. Of the illumination devices 1a and 1b of the optical detection part 54a on the front side, as shown FIG. 3, one of the light sources is the foreground illumination, that is, the light source for illuminating the window member 61a side of the color sorter on which the items-to-be-sorted, such as grains, flow down, and the other one of the light sources is the background illumination, that is, the light source for illuminating the background 60a. In a similar way, of the illumination devices 1c and 1d of the optical detection part 54b on the rear side, as shown FIG. 3, one light source is the foreground illumination, that is, the light source for illuminating the window member 61b side of the color sorter on which the items-to-be-sorted, such as grains, flow down, and the other light source is the background illumination, that is, the light source for illuminating the backgrounds 60b and 60c.

Figure 5:
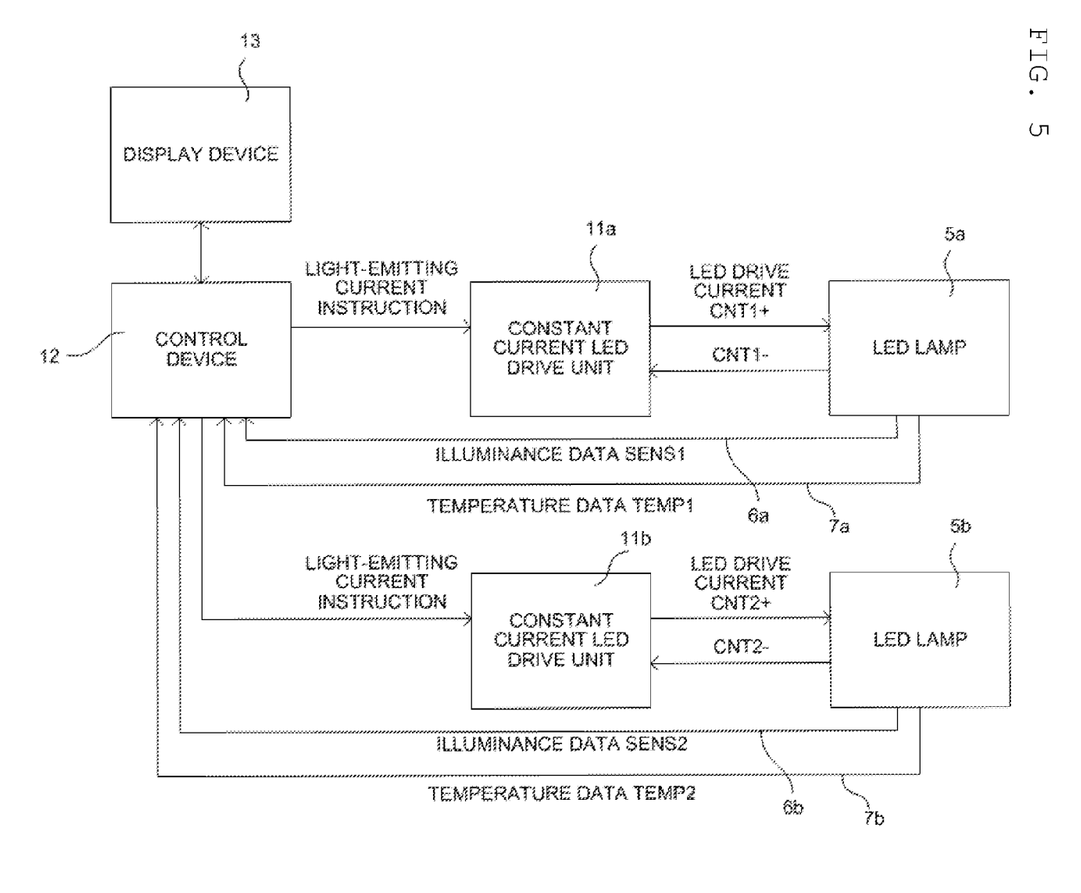
FIG. 5 is a block diagram showing a control configuration of the illumination device, which is the same as above.

FIG. 5 is a block diagram showing a control configuration of the illumination device 1. To describe the control configuration of the illumination device 1 with reference to FIG. 5, the LED substrate 3, on which the many LED elements 4 are arranged, includes: a constant current drive unit 11 that electrically connects to the LED elements 4 to supply LED drive current; a control device 12 that provides instructions to the constant current drive unit 11 to supply light-emitting current; and a display device 13 that displays various kinds of controlling details of the control device 12. To the control device 12, the illuminance sensor 6 arranged adjacent to the LED element 4 and the temperature sensor 7 arranged near the illuminance sensor 5 are electrically connected, and therefore, increase or decrease in supply of the LED drive current can be subjected to feedback control by the illuminance or the temperature near the LED element 4 when the LED elements 4 emit light.

Figure 6:
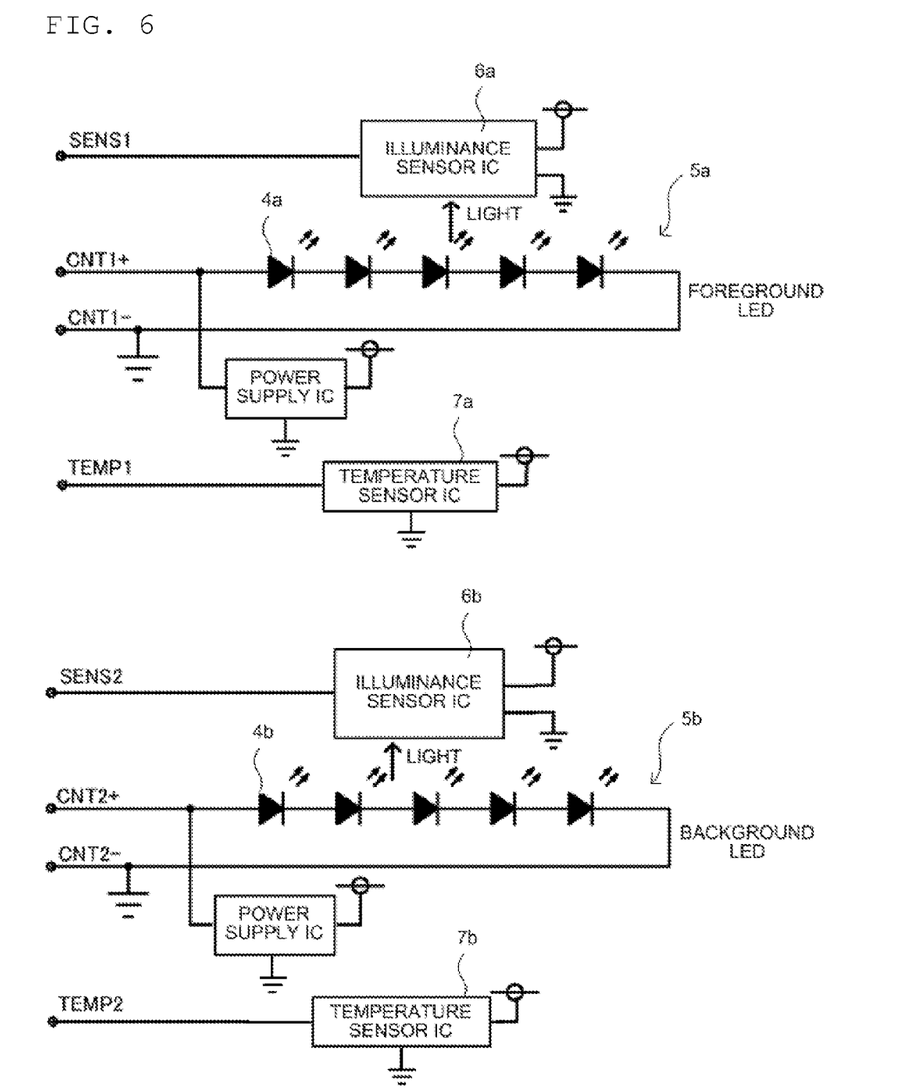
FIG. 6 is an example of a circuit diagram of the illumination device, which is the same as above.
Figure 7:
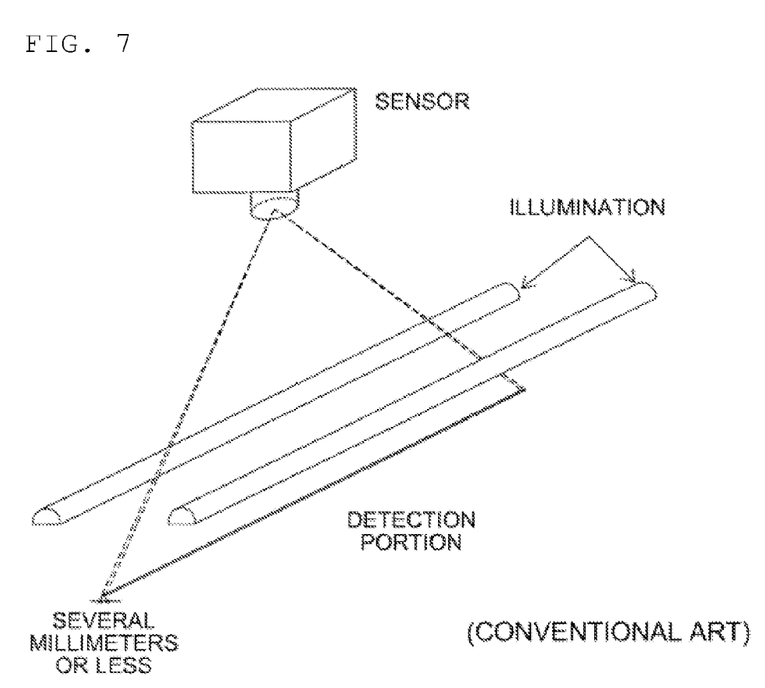
FIG. 7 is a schematic perspective view of a conventional illumination device for a color sorter.

FIG. 6 is an example of a circuit diagram of the illumination device 1. With reference to FIG. 6, many LED elements 4a are connected in series to form the light source 5a, which is the foreground illumination, and many LED elements 4b are connected in series to form the light source 5b, which is the background illumination, and each can be power-fed. At this time, when the light sources 5a and 5b emit light, the illuminance is detected by the illuminance sensors 6a and 6b, and increase or decrease in current supply is controlled to be a preset illuminance. Moreover, in causing the light sources 5a and 5b to emit light, if outputs are increased too much to be high temperature, the temperature sensors 7a and 7b operate to perform control so that current supply is reduced to become a preset temperature.

As described above, according to the embodiment, the light source 5 arranged at the optical detection part 54 is an integration of at least two light sources 5a and 5b together, and the one light source 5a illuminates the side on which the items-to-be-sorted flow down and the other light source 5b illuminates the background 60 side arranged to face the camera 59. This makes it possible to double the light source 5a that illuminate the side on which the items-to-be-sorted flow down and the light source 5b that illuminates the background 60, and to reduce the number of light sources installed in the optical detection part 54. Moreover, by performing control to increase or decrease the amount of light of the illumination on the background 60 side, adjustment of an inclination angle of the background plate 60 becomes unnecessary, and it becomes possible to perform significant downsizing and cost reduction by eliminating a driving means for changing the inclination angle.

Moreover, if one of the light sources 5a is formed as the light source that emits light in a wavelength region of visible light and the other one of the light sources 5b is formed as a light source that emits light in a wavelength region of near-infrared light, it is possible to double the light source for the visible light and the light source for the near-infrared light, and therefore, the number of light sources installed in the optical detection part 54 can be reduced.

Then, by forming the shape of the chassis 2 on which the LED substrate 3 is placed as a triangular roof shape in a cross section, one of the inclined surfaces 2c of the triangular roof shape is used for the light source 5a for illuminating the side on which the items-to-be-sorted flow down and the other one of the inclined surfaces 2d is used for the light source 5b for illuminating the background 60 arranged to face the camera 59, and accordingly, it becomes possible to downsize the shared light source and to make the shared light source less costly.

Further, even though the light source 5 is such that many LED elements 4 are linearly aligned in the longitudinal direction on the LED substrate 3, since the LED substrate 3 is mounted on the longitudinal chassis 2 for heat radiation, the LED substrate has high heat radiation effect and is less likely to be out of order. Moreover, in the LED substrate 3, while the illuminance sensor 6 is provided adjacent to the LED element 4, the control device 12 for keeping illuminance of the light source 5 constant based on illuminance data from the illuminance sensor 6 is provided, and therefore, it becomes possible to resolve troubles, such as destabilization of illuminance or excessive increase in output, due to the illuminance of the light source kept constant based on the illuminance data from the illuminance sensor 6. This makes it possible to provide the illumination device excellent in long-life, low-power and vibration-resistant properties.

Moreover, in the LED substrate 3, by providing the temperature sensor 7 that detects the temperature of the LED elements 4 near the illuminance sensor 6, accuracy in making the illuminance constant is improved. In other words, if control of increasing the illuminance based on the data from the illuminance sensor 6 is performed, the temperature of the LED elements 4 rises in proportion to increase of current. At this time, since the temperature sensor 7 operates, it becomes possible to suppress the rise of the current within an applicable temperature range of the LED elements 4.

INDUSTRIAL APPLICABILITY

The invention is applicable to an illumination device of a color sorter, and the like.

REFERENCE SIGNS LIST

1 Illumination device
2 Chassis
3 LED substrate
4 LED element
5 Light source
6 Illuminance sensor
7 Temperature sensor
8 LED lamp socket
9 Illumination part cover
10 Sensor connector
11 Constant current drive unit
12 Control device
13 Display device
50 Color sorter
51 Chute
52 Storage tank
53 Vibrating feeder
54 Optical detection part
55 Ejector nozzle
56 Acceptable item recovery trough
57 Unacceptable item recovery trough
58 Auxiliary unacceptable item recovery trough
59 Camera
60 Background
61 Window member

What is claimed is:

1. An illumination device for a color sorter comprising a longitudinal chassis for heat radiation, a pair of LED substrates placed on the chassis, a first light source in which many LED elements are linearly aligned in a longitudinal direction on one LED substrate, and a second light source in which many LED elements are linearly aligned in the longitudinal direction on the other LED substrate, wherein the first light source illuminates a side on which items-to-be-sorted flow down and the second light source illuminates a side of a background arranged to face a camera of the color sorter, one of the first light source and the second light source being a light source that emits light in a wavelength range of visible light, and another one of the first light source and the second light source being a light source that emits light in a wavelength range of near-infrared light, wherein a shape of the chassis on which the LED substrates are placed is a triangular roof shape in a cross section, and the first light source is provided on one of inclined surfaces of the triangular roof shape and the second light source is provided on the other one of the inclined surfaces, wherein an internal angle between the inclined surfaces of the triangular roof shape of the chassis is in a range of about 80° to about 100°.

2. The illumination device for a color sorter according to claim 1, wherein, in each LED substrate, while an illuminance sensor is provided adjacent to the LED element, a control device that keeps illuminance of the first or second light sources provided thereon constant based on illuminance data from the illuminance sensor is provided.

3. An illumination device for a color sorter comprising a longitudinal chassis for heat radiation, a pair of LED substrates placed on the chassis, a first light source in which many LED elements are linearly aligned in a longitudinal direction on one LED substrate, and a second light source in which many LED elements are linearly aligned in the longitudinal direction on the other LED substrate, wherein, in each LED substrate, while an illuminance sensor is provided adjacent to the LED element, a control device that keeps illuminance of the first or the second light source provided thereon constant based on illuminance data from the illuminance sensor is provided, wherein a shape of the chassis on which the LED substrate is placed is a triangular roof shape in a cross section, and the first light source is provided on one of inclined surfaces of the triangular roof shape and the second light source is provided on the other one of the inclined surfaces, wherein an internal angle between the inclined surfaces of the triangular roof shape of the chassis is in a range of about 80° to about 100°.

4. The illumination device for a color sorter according to claim 3, further comprising temperature sensor that detects a temperature of the LED elements, provided in the LED substrate near the illuminance sensor.

* * * * *